(12) United States Patent
Dieringer et al.

(10) Patent No.: US 9,339,422 B2
(45) Date of Patent: May 17, 2016

(54) ABSORBENT ARTICLE WITH RAISED BODY CONFORMING STRUCTURE

(71) Applicant: Kimberly-Clark Worldwide, Inc., Neenah, WI (US)

(72) Inventors: Jessica Annette Ives Dieringer, Neenah, WI (US); Cheri Lee Paul, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/528,550

(22) Filed: Oct. 30, 2014

(65) Prior Publication Data

US 2015/0057629 A1    Feb. 26, 2015

Related U.S. Application Data

(62) Division of application No. 13/412,169, filed on Mar. 5, 2012, now Pat. No. 8,915,899.

(51) Int. Cl.

| | | |
|---|---|---|
| *A61F 13/15* | (2006.01) | |
| *A61F 13/511* | (2006.01) | |
| *A61F 13/472* | (2006.01) | |

(Continued)

(52) U.S. Cl.
CPC ..... *A61F 13/51108* (2013.01); *A61F 13/00063* (2013.01); *A61F 13/47* (2013.01); *A61F 13/47218* (2013.01); *A61F 13/537* (2013.01); *A61F 13/5323* (2013.01); *A61F 2013/1578* (2013.01); *A61F 2013/4587* (2013.01); *A61F 2013/51023* (2013.01); *A61F 2013/51186* (2013.01); *A61F 2013/5355* (2013.01); *A61F 2013/530437* (2013.01); *A61F 2013/530445* (2013.01)

(58) Field of Classification Search
CPC .......... A61F 2013/530437; A61F 2013/51023; A61F 2013/51186; A61F 2013/4587
USPC .......................... 604/385.17, 385.01, 385.101
See application file for complete search history.

(56) References Cited

U.S. PATENT DOCUMENTS

| | | | |
|---|---|---|---|
| 4,475,913 | A | 10/1984 | Hlaban |
| 4,758,240 | A | 7/1988 | Glassman |

(Continued)

FOREIGN PATENT DOCUMENTS

| | | | |
|---|---|---|---|
| EP | 0 119 919 A1 | 9/1984 | |
| EP | 0 223 487 A2 | 5/1987 | |

(Continued)

*Primary Examiner* — Jacqueline Stephens
(74) *Attorney, Agent, or Firm* — Kimberly-Clark Worldwide, Inc.

(57) ABSTRACT

An absorbent article includes a body side liner, a back sheet, an absorbent body positioned between the body side liner and the back sheet, and a body conforming structure positioned in direct facing relation with the body side liner. The body conforming structure length is at least 50% the absorbent body length and is aligned with a longitudinal centerline of the absorbent article. The median anterior portion width of the body conforming structure is greater than the median central portion width of the body conforming structure which is greater than the median posterior portion width of the body conforming structure. The anterior portion includes a well, the central portion includes a channel, and the posterior portion includes a taper. The well transitions into the channel via a first convex transition and a concave transition. The channel transitions into the taper via a second convex transition.

16 Claims, 7 Drawing Sheets

(51) Int. Cl.
- *A61F 13/537* (2006.01)
- *A61F 13/00* (2006.01)
- *A61F 13/47* (2006.01)
- *A61F 13/532* (2006.01)
- *A61F 13/53* (2006.01)
- *A61F 13/535* (2006.01)
- *A61F 13/51* (2006.01)
- *A61F 13/45* (2006.01)

(56) References Cited

U.S. PATENT DOCUMENTS

| | | |
|---|---|---|
| D320,274 S | 9/1991 | Douglas |
| 5,057,096 A | 10/1991 | Faglione |
| 5,219,341 A | 6/1993 | Serbiak et al. |
| 5,462,541 A | 10/1995 | Bruemmer et al. |
| 5,484,430 A | 1/1996 | Osborn, III |
| 5,545,156 A | 8/1996 | Dipalma et al. |
| 5,562,680 A | 10/1996 | Hasson |
| 5,591,148 A | 1/1997 | McFall et al. |
| 5,702,380 A | 12/1997 | Walker |
| 5,743,896 A | 4/1998 | Parker |
| 5,810,798 A | 9/1998 | Finch et al. |
| 6,160,197 A | 12/2000 | Lassen et al. |
| 6,168,583 B1 | 1/2001 | Tanji et al. |
| 6,221,460 B1 | 4/2001 | Weber et al. |
| D469,868 S | 2/2003 | Bruce et al. |
| 6,562,192 B1 | 5/2003 | Hamilton et al. |
| D483,485 S | 12/2003 | Phillips-Nicholas |
| 6,660,903 B1 | 12/2003 | Chen et al. |
| 6,667,424 B1 | 12/2003 | Hamilton et al. |
| 6,700,035 B2 | 3/2004 | Yoshimasa |
| 6,929,629 B2 | 8/2005 | Drevik et al. |
| 6,965,058 B1 | 11/2005 | Raidel et al. |
| 6,984,225 B2 | 1/2006 | Raidel et al. |
| 7,156,832 B2 | 1/2007 | Drevik et al. |
| 7,160,280 B2 | 1/2007 | Bailey |
| D571,004 S | 6/2008 | Cardin et al. |
| 7,429,689 B2 | 9/2008 | Chen et al. |
| D614,765 S | 4/2010 | Webster |
| 7,754,940 B2 | 7/2010 | Brisebois et al. |
| D630,730 S | 1/2011 | Clark |
| 7,922,706 B2 | 4/2011 | Konawa |
| D646,781 S | 10/2011 | Forbes et al. |
| D673,672 S | 1/2013 | Dieringer et al. |
| D677,787 S | 3/2013 | Dieringer et al. |
| 8,439,885 B2 | 5/2013 | Sakano et al. |
| 8,915,898 B2 | 12/2014 | Dieringer et al. |
| 2003/0120242 A1 | 6/2003 | Carlos et al. |
| 2003/0153232 A1 | 8/2003 | Raidel et al. |
| 2003/0225385 A1 | 12/2003 | Glaug et al. |
| 2005/0010185 A1 | 1/2005 | Mizutani et al. |
| 2005/0059942 A1 | 3/2005 | Krautkramer et al. |
| 2006/0229580 A1 | 10/2006 | Raidel et al. |
| 2006/0276766 A1 | 12/2006 | Kentolall |
| 2007/0135787 A1 | 6/2007 | Raidel et al. |
| 2009/0204095 A1 | 8/2009 | Mcdaniel |
| 2010/0057031 A1 | 3/2010 | Kuroda et al. |
| 2010/0312216 A1* | 12/2010 | Periman .................. 604/385.04 |
| 2012/0037327 A1 | 2/2012 | Alkmin et al. |
| 2012/0040039 A1 | 2/2012 | Alkmin et al. |
| 2012/0041405 A1 | 2/2012 | Alkmin et al. |

FOREIGN PATENT DOCUMENTS

| | | |
|---|---|---|
| JP | 2006-263205 A | 10/2006 |
| KR | 10-2010-0047666 A | 5/2010 |
| WO | WO 92/07535 A1 | 5/1992 |
| WO | WO 95/16424 A1 | 6/1995 |
| WO | WO 97/09014 A1 | 3/1997 |
| WO | WO 2008/004961 A1 | 1/2008 |

* cited by examiner

ABSORBENT ARTICLE WITH RAISED BODY CONFORMING STRUCTURE

PRIORITY

This application is a divisional of application Ser. No. 13/412,169, entitled "Absorbent Article with Raised Body Conforming Structure" and filed in the U.S. Patent and Trademark Office on Mar. 5, 2012. The entirety of the prior application is hereby incorporated by reference in this application.

BACKGROUND OF THE INVENTION

Absorbent articles such as sanitary napkins, panty liners, and incontinence pads are designed to absorb and retain fluid discharges from the human body. It is desirable that such absorbent articles conform to the body of the wearer during use. An absorbent article with body conforming structure can increase the effectiveness of the absorbent article by reducing the possibility that fluids such as menses or urine will leak past the perimeter of the absorbent article. Additionally, an absorbent article with body conforming structure can also be more comfortable to wear as compared to similar absorbent articles without the body conforming structure.

Maintaining an absorbent article, such as an incontinence pad, in the proper position relative to the body of the wearer is difficult because of external forces exerted upon the absorbent article under dynamic conditions. These external forces may be a result of the attachment of the absorbent garment to the wearer's clothes or may be a result of body movement, in particular, thigh movement. In use, these forces may cause the absorbent article to pull away from the body or shift from the desired position.

Previous absorbent articles have attempted to introduce body conforming elements near the body side of the absorbent article. While these attempts have had some success, there remains a need for a raised body conforming structure which aligns with the female anatomy to intake fluid quickly, maintain a dry surface, distribute fluid effectively throughout the product, and conform to the contours of the body during use.

SUMMARY OF THE INVENTION

In one aspect, the present invention provides an absorbent article having a body side liner, a back sheet, and an absorbent body positioned between the body side liner and the back sheet wherein the absorbent body defines an absorbent body length. The absorbent article also includes a body conforming structure positioned in direct facing relation with the body side liner. The body conforming structure defines a body conforming structure length that is at least 50% the absorbent body length. The body conforming structure is aligned with a longitudinal centerline of the absorbent article. The body conforming structure defines an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width. The anterior portion includes a well, the central portion includes a channel, and the posterior portion includes a taper. The well transitions into the channel via a first convex transition and a concave transition. The channel transitions into the taper via a second convex transition.

In some embodiments of this aspect, the body conforming structure defines a longitudinal centerline and a lateral centerline wherein the body conforming structure is symmetric about the longitudinal centerline and asymmetric about the lateral centerline.

In some embodiments of this aspect, the lateral centerline divides the body conforming structure into an anterior portion having an anterior portion area and a posterior portion having a posterior portion area wherein the anterior portion area is greater than the posterior portion area.

In some embodiments of this aspect, the body conforming structure is positioned between the body side liner and the absorbent body and the body side liner is joined to the absorbent body at one or more shaping bonds located around a perimeter of the body conforming structure. In some embodiments, the body side liner is joined to the absorbent body at a plurality of shaping bonds proximate the perimeter of the body conforming structure in the posterior portion.

In some embodiments of this aspect, the absorbent article further includes a supplemental body conforming structure positioned between the body side liner and the body conforming structure. The supplemental body conforming structure defines a shape and defines an area. The body conforming structure defines a shape and defines an area. The supplemental body conforming structure shape is substantially similar to the body conforming structure shape. In some embodiments, the supplemental body conforming structure area is less than the body conforming structure area.

In some embodiments of this aspect, the body conforming structure is a discrete element positioned between the body side liner and the absorbent body and is devoid of cellulose fibers or superabsorbent. In some embodiments, the body conforming structure is made of a bonded carded web of polypropylene fibers having a based weight of at least 100 gsm.

In another aspect, the present invention provides an absorbent article having a body side liner, a back sheet, and an absorbent body positioned between the body side liner and the back sheet wherein the absorbent body defines an absorbent body length. The absorbent article further includes a body conforming structure positioned in direct facing relation with the body side liner. The body conforming structure is a nonwoven fabric that is substantially devoid of cellulose fibers and superabsorbent material. The body conforming structure defines a body conforming structure length that is at least 50% the absorbent body length. The body conforming structure is aligned with a longitudinal centerline of the absorbent article. The body conforming structure defines an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width. The anterior portion includes a well, the central portion includes a channel, and the posterior portion includes a taper. The well transitions into the channel via a first convex transition and a concave transition and wherein the channel transitions into the taper via a second convex transition.

In some embodiments of this aspect, the body conforming structure is a nonwoven fabric of bonded-carded web made of polypropylene fibers. In some embodiments, the body conforming structure has a basis weight of at least 200 gsm.

In some embodiments, the absorbent article defines a thickness and the body conforming structure defines a thickness that is at least 25% the thickness of the absorbent article.

In some embodiments, the absorbent body includes a body side absorbent layer and a retention layer positioned between the body side absorbent layer and the backsheet. The body side absorbent layer is an airlaid material and the retention layer is made of 70-90% superabsorbent material.

In some embodiments, the body conforming structure defines a longitudinal centerline and a lateral centerline wherein the body conforming structure is symmetric about the longitudinal centerline and asymmetric about the lateral centerline. The lateral centerline divides the body conforming structure into an anterior portion having an anterior portion area and a posterior portion having a posterior portion area wherein the anterior portion area is greater than the posterior portion area.

In some embodiments of this aspect, the absorbent article further includes a supplemental body conforming structure positioned between the body side liner and the body conforming structure. The supplemental body conforming structure defines a shape and defines an area. The body conforming structure defines a shape and defines an area. The supplemental body conforming structure shape is substantially the same as the body conforming structure shape and the supplemental body conforming structure area is less than the body conforming structure area.

In another aspect, the present invention provides an array of absorbent articles. The array includes a first absorbent article and a second absorbent article. The first absorbent article includes a first body side liner, a first back sheet, a first absorbent body positioned between the first body side liner and the first back sheet wherein the first absorbent body defines a first absorbent body length. The first absorbent article also includes a first body conforming structure positioned in direct facing relation with the first body side liner. The first body conforming structure is aligned with a longitudinal centerline of the first absorbent article. The first body conforming structure has a first body conforming structure length that is at least 50% the first absorbent body length. The first body conforming structure defines a first body conforming structure area, a first body conforming structure shape, an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width.

The second absorbent article includes a second body side liner, a second back sheet, a second absorbent body positioned between the second body side liner and the second back sheet wherein the second absorbent body defines a second absorbent body length. The second absorbent article also includes a second body conforming structure positioned in direct facing relation with the second body side liner and aligned with a longitudinal centerline of the second absorbent article. The second body conforming structure has a second body conforming structure length that is at least 50% the second absorbent body length. The second body conforming structure defines a second body conforming structure area, a second body conforming structure shape, an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width.

In the array of articles, the first absorbent body length is at least 10% greater than the second absorbent body length and the first body conforming structure shape is substantially the same as the second body conforming structure shape.

In some embodiments of this aspect, the first absorbent body includes a first absorbent body peripheral edge that defines a first absorbent body shape and the second absorbent body includes a second absorbent body peripheral edge that defines a second absorbent body shape that is different than the first absorbent body shape.

In some embodiments of this aspect, the array further includes a third absorbent article. The third absorbent article includes a third body side liner, a third back sheet, a third absorbent body positioned between the third body side liner and the third back sheet. The third absorbent body includes an opening and defines a third absorbent body length. The opening defines an opening area, an opening shape, an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width. The opening includes a peripheral edge that defines an opening shape that is substantially the same as the first body conforming structure shape and the second body conforming structure shape.

In some embodiments of this aspect, the third absorbent body defines a third absorbent body length and the opening defines an opening length that is at least 50% the third absorbent body length.

DETAILED DESCRIPTION OF THE DRAWINGS

The disposable absorbent articles of the present invention include a body conforming structure which aligns with the female anatomy and is believed to improve fit, comfort, dryness, and leakage performance. The body conforming structure has a geometry which aligns an anterior portion of the body conforming structure with the urethra, a central portion of the body conforming structure with the labia and pelvic floor, and a posterior portion of the body conforming structure with the gluteal cleft. The body conforming structure is adapted to accept and temporarily hold urine insults to minimize run-off. In use, the body conforming structure quickly becomes saturated and thus distributes the urine across a wide surface area of the absorbent article. The relatively narrow width of the body conforming structure is believed to minimize the compressive forces generated by upper thigh movement which could reduce void volume. The saturated body conforming structure is then desorbed into the absorbent body resulting in a relatively dry surface proximate the body.

Figure 1:
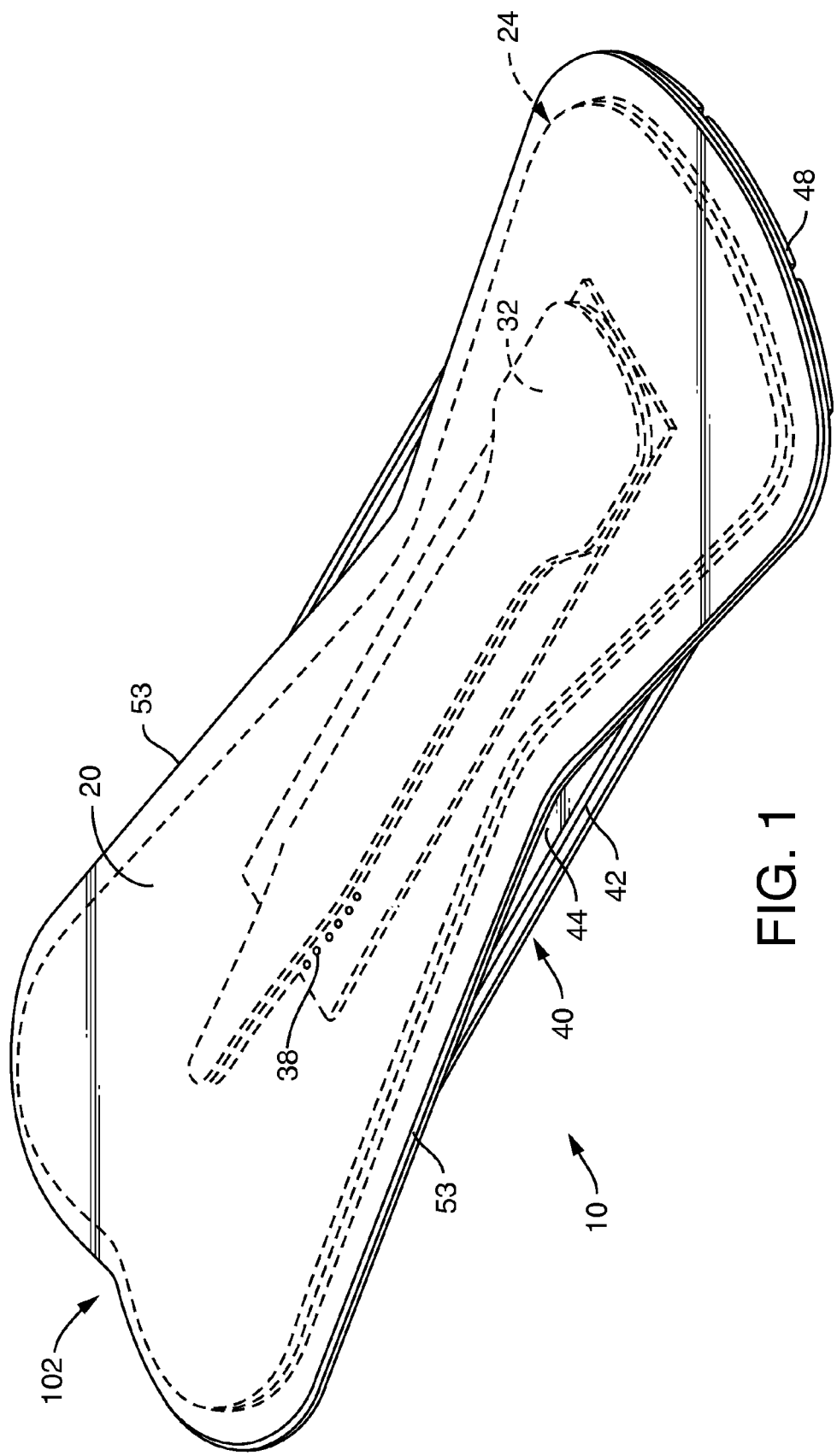
FIG. 1 representatively illustrates a top perspective view of an embodiment of the present invention.
Figure 2:
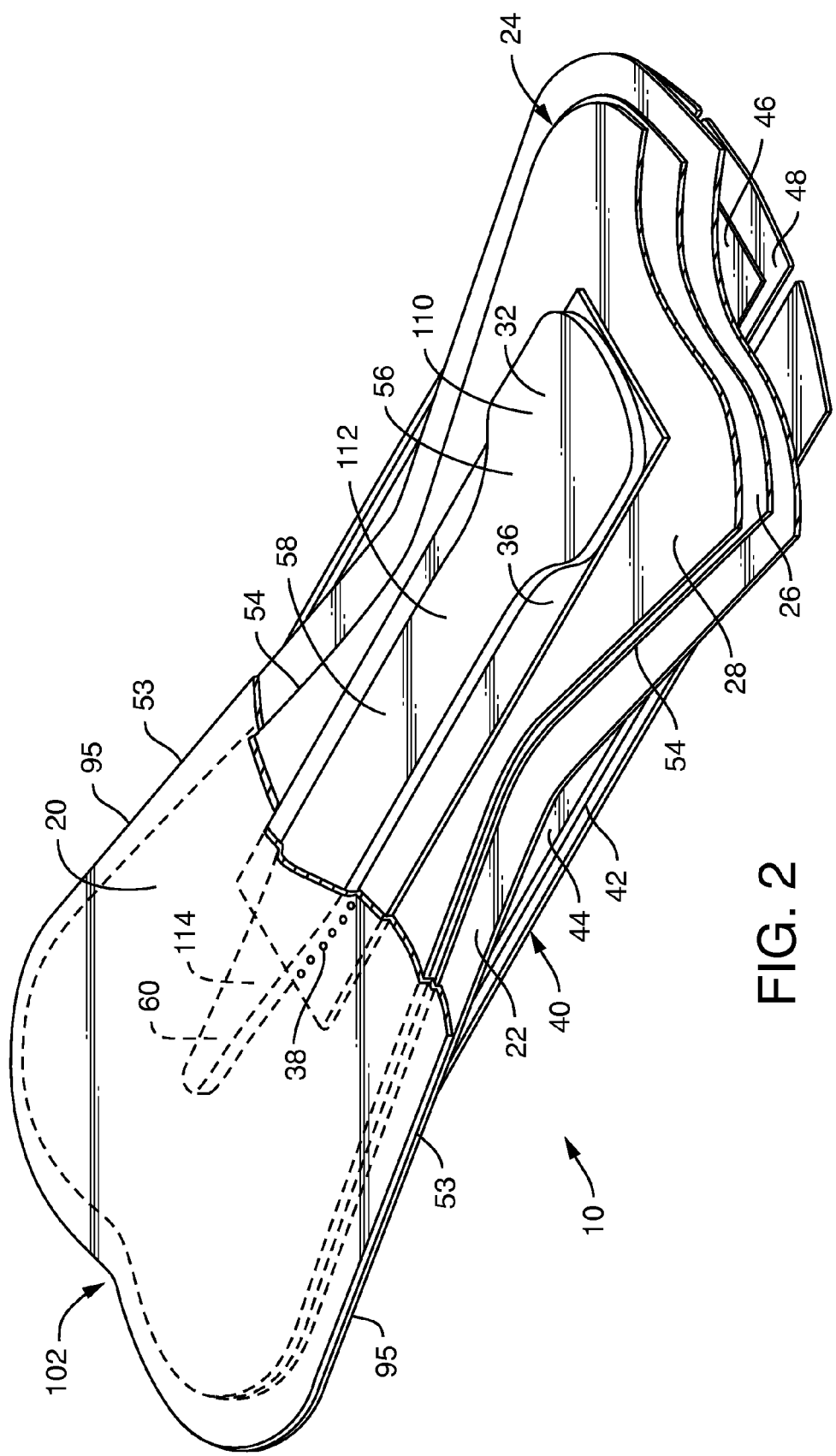
FIG. 2 representatively illustrates a top perspective view of the embodiment of FIG. 1 with portions cut away to illustrate underlying structure.
Figure 3:
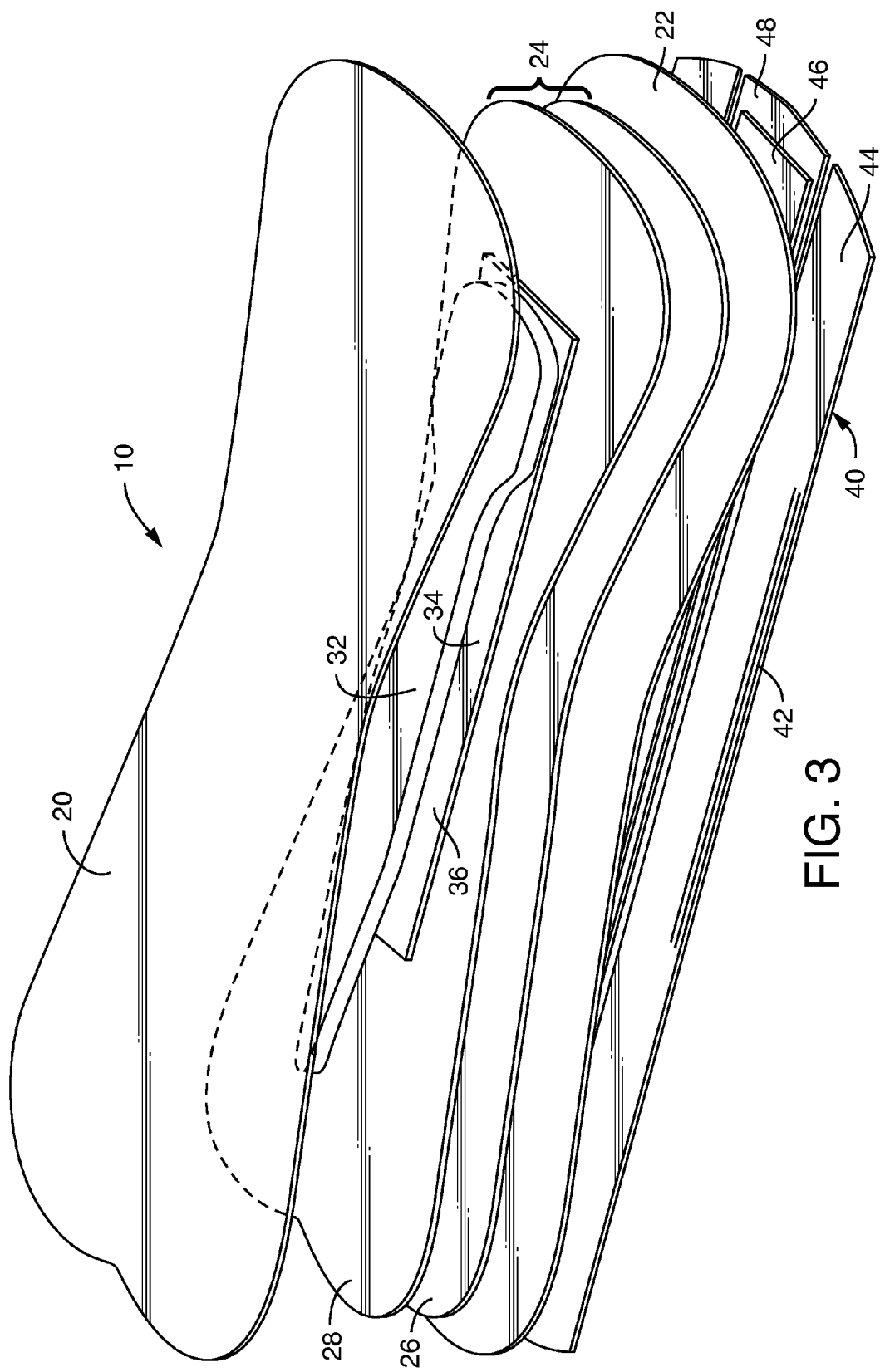
FIG. 3 representatively illustrates an expanded perspective view of the embodiment of FIG. 1.
Figure 4:
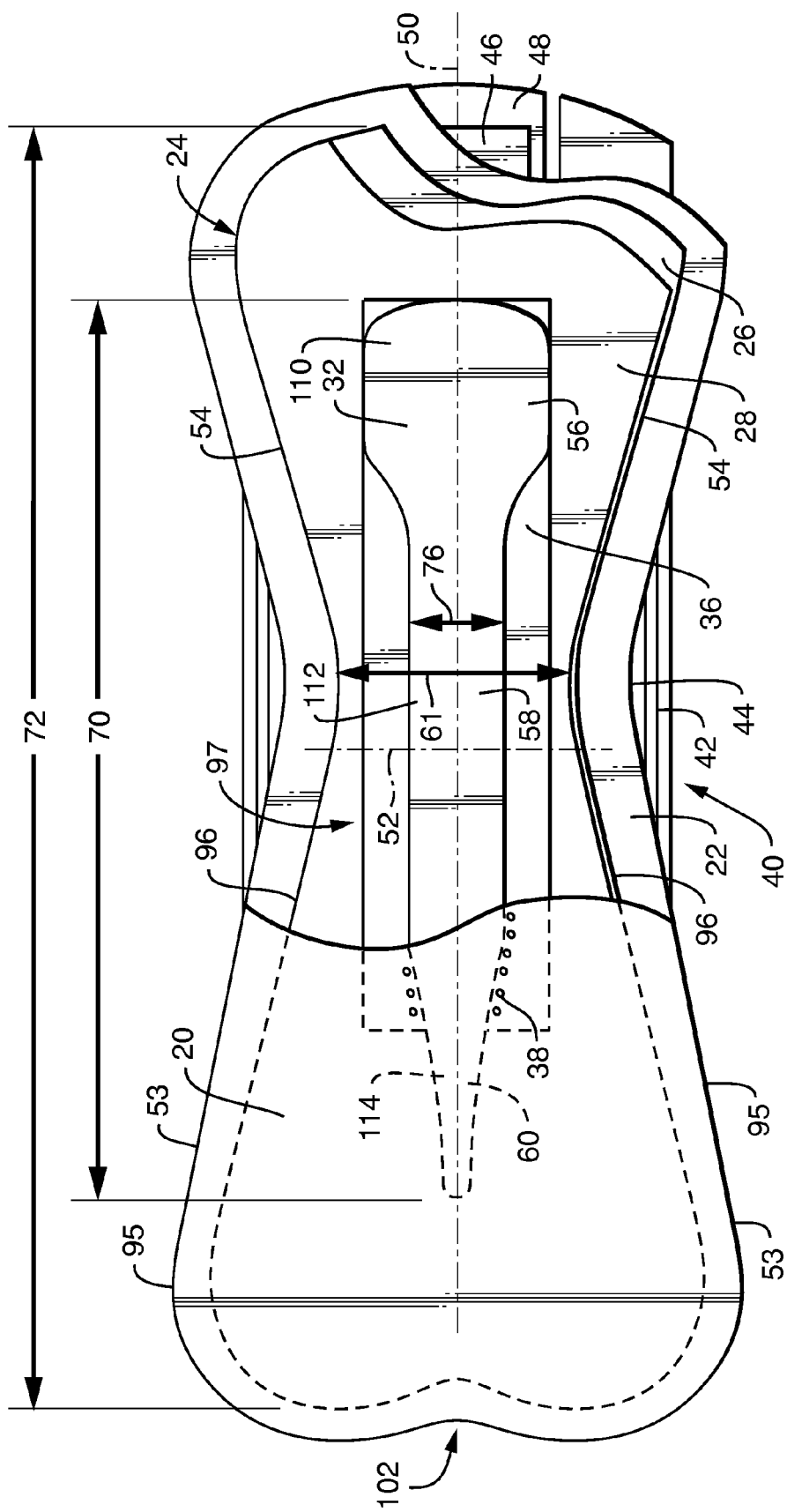
FIG. 4 representatively illustrates a top plan view of the embodiment of FIG. 1 with portions cut away to illustrate underlying structure.

FIGS. 1-4 representatively illustrate a first embodiment of a disposable absorbent article 10 of the present invention. FIG. 1 is a top perspective view of the absorbent article 10. FIG. 2 is a top perspective view of the absorbent article 10 of FIG. 1 with portions cut away to illustrate underlying structure. FIG. 3 is an expanded view of the absorbent article 10 of FIG. 1. FIG. 4 is a top plan view of the absorbent article 10 of FIG. 1 with portions cut away to reveal underlying structure. The absorbent article 10 includes a liquid-permeable topsheet (also referred to as a body side liner) 20, a substantially liquid-impermeable back sheet 22, and an absorbent body 24 positioned between the back sheet 22 and the topsheet 20. The absorbent article 10 further includes a body conforming structure 32 in facing relation with the topsheet 20. In some embodiments, the topsheet may be located between the body conforming structure and the back sheet (not shown). In other embodiments, the body conforming structure 32 may be located between the topsheet 20 and the absorbent body 24 as illustrated. In some embodiments, the absorbent articles of the present invention may further include containment flaps, garment attachment adhesive, a peel strip, or combinations thereof. For example, the absorbent article 10 illustrated in FIGS. 1-4 includes containment flaps 40 which in turn include containment elastics 42 and a containment flap carrier web 44. Likewise, the absorbent article 10 of FIGS. 1-4 is shown with an optional garment attachment adhesive 46 applied to the back sheet 22 and covered with a peel strip 48.

In various embodiments, the absorbent body 24 may consist of a single layer of material or may consist of two or more layers of material. For example, the absorbent body 24 may consist of two layers of material as illustrated in FIG. 3. Specifically, the absorbent body 24 may include a retention layer 26 and a body side absorbent layer 28. The retention layer 26 may be positioned towards the back sheet 22 and the body side absorbent layer 28 may be superposed over the retention layer 26 and positioned towards the topsheet 20 as illustrated. In other embodiments, the relative orientation of the retention layer and the body side absorbent layer may be reversed (not illustrated). Whether a single layer or multiple layers, the absorbent body defines an absorbent body length, an absorbent body width, and an absorbent body perimeter. The absorbent body perimeter further defines an absorbent body area. In embodiments wherein the absorbent body includes two or more layers, the absorbent body length, the absorbent body width, the absorbent body perimeter, and the absorbent body area are defined by the furthest extent, in the plane defined by the longitudinal direction and the lateral direction, of any of the layers.

Figure 5:
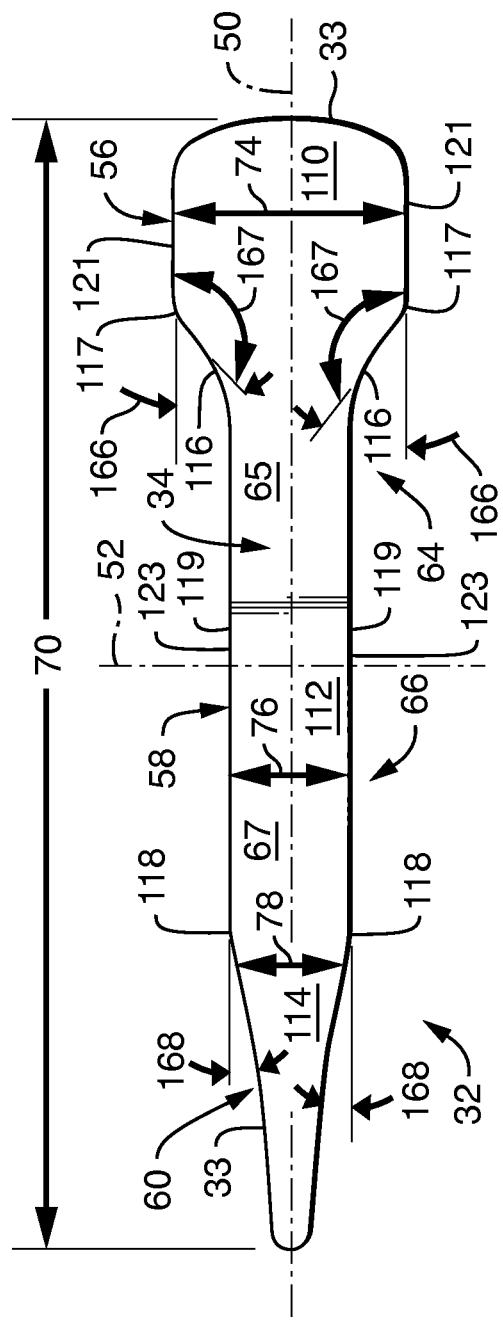
FIG. 5 representatively illustrates a top plan view of the body conforming structure of FIGS. 1-4.

Referring now to FIG. 5, a top plan view of the body conforming structure 32 of FIGS. 1-4 is representatively illustrated. The body conforming structure 32 defines a peripheral edge 33 and defines an area 34. In various embodiments, the body conforming structure 32 may be symmetrical about a longitudinal centerline 50. In some embodiments, the body conforming structure 32 may be asymmetrical about a lateral centerline 52. For example, as illustrated in FIG. 5, the body conforming structure 32 is symmetrical about the longitudinal centerline 50 and asymmetrical about the lateral centerline 52.

The lateral centerline 52 divides the body conforming structure into an anterior half 64 and a posterior half 66. The anterior half 64 defines an anterior half area 65 and the posterior half 66 defines a posterior half area 67. As used herein, the term "anterior" refers to the portion of the structure, layer, or article that is adapted to be oriented towards the front of the wearer in normal use. Likewise, as used herein, the term "posterior" refers to the portion of the structure, layer, or article that is adapted to be oriented towards the back of the wearer in normal use. In various embodiments, the anterior half area 65 is greater than the posterior half area 67.

The body conforming structures 32 of the present invention also define an anterior portion 56, a posterior portion 60, and a central portion 58 positioned between the anterior portion 56 and the posterior portion 60. The anterior portion 56 is defined as the anterior third of the body conforming structure, the central portion 58 is defined as the middle third of the body conforming structure, and the posterior portion 60 is defined as the posterior third of the body conforming structure, all as measured relative to the longitudinal centerline 50.

The absorbent articles of the present invention may include lateral side edges of any suitable shape. For example, the lateral side edges may be straight or may have arcuate shapes such as concave curves, convex curves, or combinations thereof. Referring again to FIGS. 1 and 4, the absorbent article 10 is illustrated with lateral side edges 53 that are concave. The combination of the two lateral side edges 53 in this embodiment combine to create a curved shape. Likewise, the absorbent body of the present invention may include lateral side edges of any suitable shape. For example, the lateral side edges of the absorbent body may be straight or may have arcuate shapes, such as concave curves, convex curves, or combinations thereof. Likewise, one or more of the layers of the absorbent body may include lateral side edges that are straight, concave, convex, or combinations thereof. For example, referring now to FIG. 4, the bodyside absorbent layer 28 and the retention layer 26 are both illustrated with lateral side edges 54 that are concave. The concave lateral side edges 54 define a minimum width 61.

In some embodiments, the minimum width of the bodyside absorbent layer is generally aligned with the lateral centerline of the body conforming structure (not illustrated). In some embodiments, the minimum width 61 of the bodyside absorbent layer 28 is aligned between the lateral centerline of the body conforming structure 32 and the anterior portion 56 of the body conforming structure 32 as illustrated in FIG. 4.

As illustrated, the anterior portion 56 of the body conforming structure 32 includes a well portion 110 that is generally rectangular in shape and has a relatively wide lateral dimension. In use, the well portion 110 is adapted to be positioned adjacent to the user's urethra. This positioning in conjunction with this shaping of the well portion 110 is believed to minimize folding of the absorbent article in this region and thereby preserve the void volume of the well portion 110 to receive body fluids.

Likewise, the central portion 58 of the body conforming structure 32 includes a channel portion 112 that is generally rectangular in shape and has a longitudinal dimension that is greater than the lateral dimension. In use, the channel portion 112 is adapted to be positioned proximate the labia. This positioning in conjunction with this shaping of the channel portion 112 is believed to allow compression of the absorbent article 10 by the user's legs while still allowing fluid to move freely between the anterior portion 56 and the posterior portion 60.

The posterior portion 60 of the body conforming structure 32 includes a taper portion 114 that is generally shaped like an acute triangle in which the smallest of the three angles is located at the posterior end of the shape. In various embodiments, the taper portion 114 may come to a relatively sharp corner (not illustrated) or may come to a more rounded corner like illustrated in FIG. 5. In use, the taper portion 114 is adapted to be positioned proximate the gluteal cleft. This positioning in conjunction with this shaping of the taper portion 114 is believed to promote a longitudinal peak in the posterior portion of the absorbent article that aligns with the gluteal cleft.

The transition between the well portion and the channel portion is marked by a distinct but gentle change in curvature. In some embodiments, the longitudinal edges 119 of the well portions 110 include sections 121 that are generally parallel to the longitudinal centerline 50. Likewise, in some embodiments, the longitudinal edges 119 of the channel portions 112 include sections 123 that are generally parallel to the longitudinal centerline 50. In these and other embodiments, the well portions 110 transition into the channel portions 112 with both a first convex transition 117 and a concave transition 116 along both longitudinal edges 119. The first convex transition 117 may define any suitable angle 167. In some embodiments, the angle 167 may be 110 to 160 degrees, 120 to 150 degrees, or about 135 degrees. Likewise, the concave transition 116 may define any suitable angle 166. In some embodiments, the angle 166 may be 30 to 60 degrees, 40 to 50 degrees, or about 45 degrees. It is believed that these transitions and these angles create localized deformation regions that act as stress concentrators. In use, the absorbent articles tend to create gentle bends proximate the stress concentrators and thus facilitate conformance of the article to the body at that position.

The transition between the channel portion and the taper portion is also marked by a distinct change in curvature. For example, the channel portions 112 transition into the taper portions 114 at a second convex transition 118 along both longitudinal edges 119. The second convex transition 118 may define any suitable angle 168. In some embodiments, the angle 168 may be 5 to 30 degrees, 10 to 20 degrees, or about 10 degrees. These transitions are also believed to create localized deformation regions that act as stress concentrators. In use, the concave transitions 116 and the convex transitions 118 are believed to promote gentle controlled bending of the absorbent article at the location of the stress concentrators. This controlled bending further allows the absorbent article to conform to the wearer's body and allows the well portion, the channel portion, and the taper portion to be properly aligned with the user's body.

In some embodiments, the absorbent article 10 may have a perimeter 95 of any suitable shape as discussed above. For example, in some embodiments, the perimeter 95 may include a concave dip 102 in the posterior section of the absorbent article 10 as illustrated in FIGS. 2 and 4. In some embodiments, the concave dip 102 may be substantially aligned with the longitudinal centerline of the body conforming structure 32 to promote a longitudinal peak in the posterior portion of the absorbent article 10 during use.

Referring to FIG. 5, the body conforming structure 32 has a first body conforming structure length 70. Likewise, the body side absorbent layer 28 has a body side absorbent length 72 as illustrated in FIG. 4. In a first embodiment, the body side absorbent length 72 may be 160 to 190 mm, 170 to 180 mm, or about 175 mm. In these embodiments, the body conforming structure length 70 may be 110 to 135 mm, 115 to 125 mm, or about 120 mm. In a second embodiment, the body side absorbent length 72 may be 235 to 265 mm, 245 to 255 mm, or about 250 mm. In these embodiments, the body conforming structure length 70 may be 165 to 190 mm, 175 to 185 mm, or about 180 mm. In a third embodiment, the body side absorbent length 72 may be 275 to 305 mm, 280 to 300 mm, or about 290 mm. In these embodiments, the body conforming structure length 70 may be 190 to 215 mm, 200 to 210 mm, or about 205 mm. In a fourth embodiment, the body side absorbent length 72 may be 325 to 355 mm, 335 to 345 mm, or about 340 mm. In these embodiments, the body conforming structure length 70 may be 225 to 250 mm, 235 to 245 mm, or about 240 mm. In various embodiments, the body conforming structure length 70 may be at least 50%, at least 60%, or at least 70% of the body side absorbent length 72. In some embodiments, the body conforming structure length 70 may be 65-75% of the body side absorbent length 72.

The body conforming structure 32 has a body conforming structure width. The body conforming structure width may be variable along the longitudinal centerline 50. For example, the body conforming structure 32 defines a median anterior portion width 74, a median central portion width 76, and a median posterior portion width 78. As used herein, the "median width" of a given portion is the numeric value separating the higher half of the widths within a given portion from the lower half of the widths within the same portion. The median width can be determined by measuring the width of a given portion at 1 mm intervals along the longitudinal centerline, arranging the measured values from lowest to highest and selecting the middle value. If there is an even number of measurements, then the median width is the average of the middle two measurements. In some embodiments, the median anterior portion width 74 is greater than the median central portion width 76, which is greater than the median posterior portion width 78. In some embodiments, the median anterior portion width 74 may be 40-60 mm, 45-55 mm, or about 52 mm. In some embodiments, the median central portion width 76 may be 10-40 mm, 20-30 mm, or about 27 mm. In some embodiments, the median posterior portion width 78 may be 7-30 mm, 10-20 mm, or about 15 mm.

The body side absorbent layer 28 also defines a minimum width 61. In the first embodiment, the minimum width 61 may be 40 to 65 mm, 45 to 60 mm, or about 55 mm. In the second embodiment, the third embodiment, and the fourth embodiment, the minimum width 61 may be 50 to 75 mm, 55 to 65 mm, or about 60 mm. In some embodiments, the median central portion width 76 of the body conforming structure 32 is 25-50% the minimum width 61 of the body side absorbent layer 28. In some embodiments, the median central portion width 76 of the body conforming structure 32 is 40-45% the minimum width 61 of the body side absorbent layer 28.

The body conforming structure 32 defines a body conforming structure peripheral edge 33 which in turn defines a body conforming structure area 34. Likewise, the body side absorbent layer 28 defines an outer perimeter 96 and the outer perimeter 96 defines a body side absorbent area 97. In the first embodiment, the body side absorbent area 97 may be 90 to 110 cm$^2$, 95 to 105 cm$^2$, or about 100 cm$^2$. In these embodiments, the body conforming structure area 34 may be 30 to 40 cm$^2$, 32 to 36 cm$^2$, or about 34 cm$^2$. In the second embodiment, the body side absorbent area 97 may be 180 to 210 cm$^2$, 190 to 200 cm$^2$, or about 195 cm$^2$. In these embodiments, the body conforming structure 34 may be 30 to 45 cm$^2$, 35 to 40 cm$^2$, or about 39 cm$^2$. In the third embodiment, the body side absorbent area 97 may be 220 to 260 cm$^2$, 230 to 250 cm$^2$, or about 240 cm$^2$. In these embodiments, the body conforming structure 34 may be 40 to 55 cm$^2$, 45 to 50 cm$^2$, or about 48 cm$^2$. In the fourth embodiment, the body side absorbent area 97 may be 300 to 345 cm$^2$, 310 to 335 cm$^2$, or about 325 cm$^2$. In these embodiments, the body conforming structure 34 may be 55 to 75 cm$^2$, 60 to 70 cm$^2$, or about 65 cm$^2$. In various embodiments, the body conforming structure area 34 may be at least 15%, at least 20%, or at least 30% the body side absorbent area 97. In some embodiments, the body conforming structure 34 may be about 20% the body side absorbent area 97.

In some embodiments, the absorbent article of the present invention may also include a supplemental body conforming structure. For example, referring now to FIG. 6, an absorbent article 80 is illustrated. The absorbent article 80 includes a liquid-permeable topsheet (also referred to as a body side liner) 20, a substantially liquid-impermeable back sheet 22, and an absorbent body 24 positioned between the back sheet 22 and the topsheet 20. In the illustrated embodiment, the absorbent body 24 includes an absorbent pledget 26 and a body side absorbent layer 28. In other embodiments, the absorbent body 24 may include a single layer or more than two layers as discussed herein (not illustrated). The absorbent article 80 is also illustrated with optional containment flaps 40, containment elastics 42, containment flap carrier web 44, garment attachment adhesive 46, and a peel strip 48.

Figure 6:
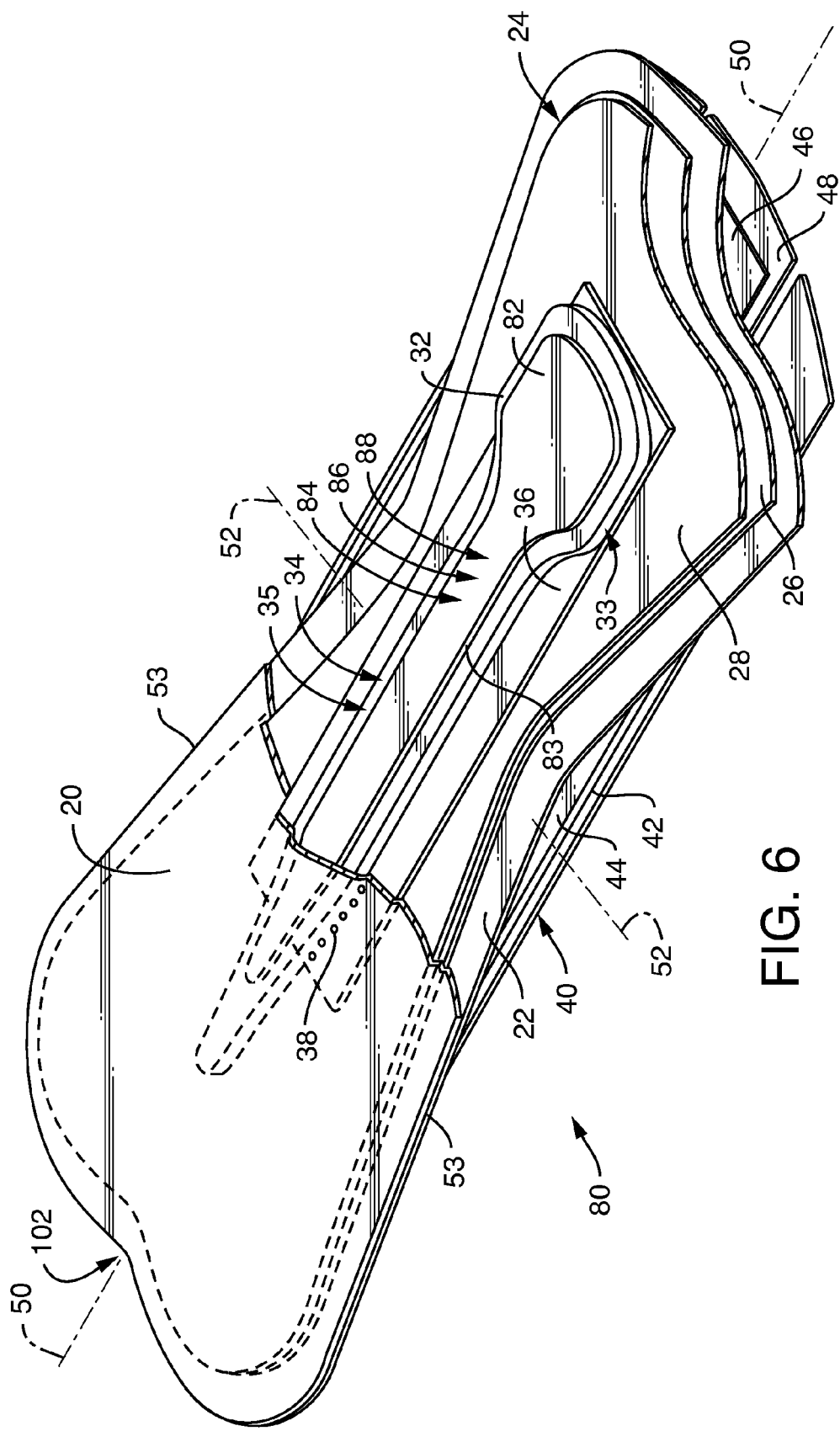
FIG. 6 representatively illustrates a top perspective view of another embodiment of the present invention with portions cut away to illustrate underlying structure.

The absorbent article 80 of FIG. 6 includes a body conforming structure 32 and a supplemental body conforming structure 82. Together, the body conforming structure 32 and the supplemental body conforming structure 82 define a composite body conforming structure 88. The body conforming structure 32 defines a body conforming structure peripheral edge 33 and defines a body conforming structure area 34. Likewise, the supplemental body conforming structure 82 defines a supplemental body conforming peripheral edge 83 and defines a supplemental body conforming structure area 84. In various embodiments, the body conforming structure area 34 may be less than or equal to the supplemental body conforming structure area 38 (not illustrated). In some embodiments, the body conforming structure area 34 is greater than the supplemental body conforming structure area 84 as illustrated in FIG. 6. In some embodiments, also as illustrated in FIG. 6, the body conforming structure 32 and the supplemental body conforming structure 82 are aligned and concentric so as to form a composite body conforming structure 88 with graduated side walls which are believed to facilitate closer alignment and conformance with the female anatomy.

The body conforming structure peripheral edge 33 also defines a body conforming structure shape 35. Likewise, the supplemental peripheral edge 83 also defines a supplemental body conforming structure shape 86. In various embodiments, the body conforming structure or the supplemental body conforming structure may have any suitable shape. In some embodiments, the body conforming structure may have a shape that is different than the shape of the supplemental body conforming structure (not illustrated). In some embodiments, the body conforming structure shape 35 may be the same or substantially the same as the supplemental body conforming structure shape 86 as illustrated in FIG. 6.

In various embodiments, the body conforming structure 32 and/or the supplemental body conforming structure 82 may be symmetrical about a longitudinal centerline 50. In some embodiments, the body conforming structure 32 and/or the supplemental body conforming structure 82 may be asymmetrical about a lateral centerline 52. For example, as illustrated in FIG. 6, the body conforming structure 32 and the supplemental body conforming structure 82 are both symmetrical about the longitudinal centerline 50 and both are asymmetrical about the lateral centerline 52.

In some embodiments, the absorbent article of the present invention may also include an optional surge layer. For example, referring again to FIG. 2, the absorbent article 10 is illustrated with a surge layer 36 positioned between the body conforming structure 32 and the body side absorbent layer 28.

In some embodiments, the absorbent article of the present invention may also include shaping bonds. For example, referring again to FIG. 2, the absorbent article 10 may include shaping bonds 38 located proximate the body conforming structure 32. In various embodiments, the shaping bonds may partially or completely surround the body conforming structure. For example, as illustrated in FIG. 2, the shaping bonds 38 partially surround the posterior portion 60 of the body conforming structure 32. The shaping bonds 38 are believed to create stress concentrators and may further enhance the body conformance and bend of the articles at desired locations. Additionally, the shaping bonds 38 may be used to closely drape the top sheet 20 around the body conforming structure 32 to maintain the distinct shape of the body conforming structure 32 and facilitate alignment and conformance of the absorbent article 10 to the body of the wearer.

The shaping bonds 38 may be any suitable size and may have any suitable spacing. In some embodiments, the shaping bonds 38 may be used to join the top sheet 20 to the body conforming structure 32, the optional surge layer 36, the body side absorbent layer 28, the retention layer 26, or the back sheet 22, or any combination thereof. In various embodiments, the shaping bonds 38 may be formed using adhesive bonding, pressure bonding, ultrasonic bonding, heat bonding, shear bonding, mechanical bonding, and the like, and combinations thereof.

In various embodiments, the body conforming structures of the present invention may further include one or more embossments. In various embodiments, the embossments may be in any suitable location, orientation, and depth. In some embodiments, the embossments may be generally aligned with the longitudinal centerline 50 of the absorbent article 10. The embossments may be formed using any suitable method such as an embossing roll having any desired pattern on the surface thereof. In various embodiments, the body conforming structure 32 may be embossed independently. In other embodiments, the body conforming structure 32 may be embossed in conjunction with the body side liner 20, the optional surge 36, the absorbent body 24, the body side absorbent layer 28, the back sheet 22, or any combination thereof. In some embodiments, the top sheet 20, the body conforming structure 32, the optional surge 36, and the body side absorbent layer 28 may be embossed together with a longitudinally oriented and centered embossment.

In various embodiments, the liquid permeable top sheet 20 may be made from any suitable material or combination of materials that are adapted to handle menses and/or urine. The top sheet 20 may include a layer constructed of any operative material, and may be a composite material. The top sheet 20 can include a woven fabric, a nonwoven fabric, a polymer film, a film-nonwoven fabric laminate or the like, as well as combinations thereof. An exemplary top sheet material is a 20 gsm spunbond web made of 100% polypropylene fibers. In various embodiments, the top sheet material may be treated with a hydrophilic wetting agent.

The substantially liquid-impermeable back sheet 22 may be made from any suitable material or combination of materials. For example, the back sheet 22 may include a polymeric film, a woven fabric, a nonwoven fabric, or the like, as well as combinations or composites thereof. For example, the back sheet may include a polymer film laminated to a woven or nonwoven fabric. In a particular feature, the polymer film can be composed of polyethylene, polypropylene, polyester or the like, as well as combinations thereof. An exemplary back sheet may include 0.9 mil polyethylene film.

The body conforming structure 32 and/or the supplemental body conforming structure 82 may be any suitable material adapted for receiving surges of urine. The body conforming structure 32 and/or the supplemental body conforming structure 82 may be a single layer of material or multiple layers of material. In various embodiments, the body conforming structure 32 and/or the supplemental body conforming structure 82 are discrete materials positioned proximate the absorbent body. In other words, in various embodiments, the body conforming structure 32 and/or the supplemental body conforming structure 82 are not formed as part of the absorbent body. Suitable body conforming structures 32 and/or supplemental body conforming structures 82 are taught in U.S. Pat. No. 5,562,650 to Everett et al., the entirety of which is incorporated herein where not contradictory.

In some embodiments the body conforming structure 32 and/or the supplemental body conforming structure 82 may be a single layer of 128 gsm bonded-carded web with through air bonded hollow polypropylene fibers. In some embodiments, the body conforming structure 32 may include two layers of a 128 gsm bonded-carded web with through air bonded hollow polypropylene fibers. In these embodiments, the body conforming structure 32 may be positioned over an optional surge layer having a single layer of 128 gsm bonded-carded web with through air bonded hollow polypropylene fibers. In some embodiments, the body conforming structure 32 may have a basis weight of at least 100, 150, 200, 250, or 300 gsm.

In some embodiments, the body conforming structure 32 alone, or the combination of the body conforming structure 32 and the supplemental body conforming structure 82, may have a thickness of 2-8 mm, 3-7 mm, or 4-6 mm. In these embodiments, the absorbent article 10 may have a whole article thickness of 10 to 13 mm, 11 to 12 mm, or about 11.5 mm. Thus, in some embodiments, the body conforming structure 32 may have a thickness that is at least 15, 20, 25, 30, 35, 40, 45, or 50% the thickness of the entire absorbent article 10. As used herein, the "thickness" of an element or an article is determined by using a 44 by 125 mm (1.75 by 5 inch) acrylic block with a mass of 120 grams in conjunction with a digital indicator. The digital indicator is aligned with the acrylic block's center point and zeroed prior to insertion of the article or element being measured. The acrylic block is centered over the body conforming structure 32 with the long dimension aligned with the longitudinal centerline of the article or element being measured. The thickness of the body conforming structure 32 alone, or the combination of the body conforming structure 32 and the supplemental body conforming structure 82, is determined by removing the respective layer or layers from the absorbent article and centering the acrylic block over said layers with the long dimension aligned with the longitudinal centerline of the layers being measured.

In various embodiments, the body conforming structure 32 and/or the supplemental body conforming structure 82 may be devoid or substantially devoid of absorbent fibers. For example, in some embodiments, the body conforming structure 32 and/or the supplemental body conforming structure 82 may be devoid, or substantially devoid, of cellulose fibers. In some embodiments, the body conforming structure 32 and/or the supplemental body conforming structure 82 may be devoid, or substantially devoid, of superabsorbent material. In some embodiments, the body conforming structure 32 and/or the supplemental body conforming structure 82 may be nonwoven fabrics such as spunbond webs, meltblown webs, airlaid webs and bonded-carded webs composed of synthetic polymer fibers. Suitable fibers include for example, polyester fibers, polypropylene fibers, polyester/polyethylene bicomponent fibers, polypropylene/polyethylene bicomponent fibers and the like, as well as blends and other combinations thereof. In various embodiments, the body conforming structure 32 and/or the supplemental body conforming structure 82 may be at least 90 or at least 95% synthetic polymer fibers. In various embodiments, the body conforming structure 32 and/or the supplemental body conforming structure 82 may be composed of a substantially hydryophobic material, and the hydrophobic material may optionally be treated with a surfactant or otherwise processed to impart a desired level of wettability and hydrophilicity.

The material used for the retention layer 26 may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In some embodiments, the retention layer 26 is a matrix of cellulosic fluff and superabsorbent hydrogel-forming particles. In addition, the retention layer may be wrapped by a liquid permeable wrapsheet to maintain the integrity when wet and to inhibit migration of absorbent materials.

The cellulosic fluff may comprise a blend of wood pulp fluff. The superabsorbent material may be present in the absorbent in an amount of from about 0 to about 90 weight percent based on total weight. The absorbent material may have a density within the range of about 0.1 to about 0.45 grams per cubic centimeter. In some embodiments the density is greater than 0.25 g/cc. Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and suitably is capable of absorbing more than about 25 times its weight in liquid. Suitable superabsorbent materials are readily available from various suppliers.

In addition to cellulosic fibers and superabsorbent materials, the retention layer may also contain adhesive elements and/or synthetic fibers that provide stabilization and attachment when appropriately activated. Additives such as adhesives may be of the same or different aspect from the cellulosic fibers; for example, such additives may be fibrous, particulate, or in liquid form; adhesives may possess either a curable or a heat-set property. Such additives can enhance the integrity of the bulk absorbent structure, and alternatively or additionally may provide adherence between facing layers of the folded structure.

The retention layer 26 may be a single layer of absorbent materials or may be a multilayer structure. Each of the layers can contain similar materials or different materials. The retention layer 26 may be partially or wholly wrapped or encompassed by a suitable tissue or nonwoven wrap that aids in maintaining the integrity and shape of the pad. One suitable wrapsheet is 12 gsm wettable spunbond-meltblown-spunbond laminate.

The bodyside absorbent layer 28 may be a single layer of absorbent material or may be a multiple layer structure. In some embodiments, the bodyside absorbent layer 28 may be made with the same materials as described above with regard to the retention layer 26. In some embodiments, the bodyside absorbent layer 28 is a thermally-bonded, stabilized airlaid fibrous web such as 100 gsm airlaid. In some embodiments, the absorbent body may include a body side absorbent layer having 30-50% or about 40% superabsorbent material in combination with a retention layer having 50-70% or about 60% superabsorbent material. In other embodiments, the absorbent body may include a body side absorbent layer having 100% airlaid fibers in combination with a retention layer having 70-90% or about 80% superabsorbent material.

The garment attachment adhesive 46 may be applied to the garment side of the backsheet 22. The garment attachment adhesive 46 may be composed of any suitable adhesive. For example, the garment attachment adhesive 46 may be a pressure-sensitive adhesive such as EASYMELT 34-5602, available from National Starch and Chemical Company.

The peel strip 48 may be added to cover the garment attachment adhesive 46 to prevent adhesive contamination. Examples of suitable peel sheets 48 include a silicone coated Kraft paper, a silicone coated film, or the like. Other release coatings include coatings containing polytetrafluoroethylene.

The containment flaps 40 of the present invention may consist of a carrier web 44, elastic elements 42, and construction adhesive (not shown). The flap carrier web 44 is desirably constructed of a liquid impermeable material, but may instead be constructed of a liquid permeable material. An example of an acceptable carrier web is a 26.5 gsm spunbond web made of polypropylene fibers. A wide variety of elastic materials may be used for the flap elastic members 42. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

In some aspects, any of the various absorbent articles with the various body conforming structures described herein may be part of one or more arrays of products. For example, referring now to FIG. 7, a first array 130 of products is representatively illustrated. The first array 130 includes a first absorbent article 132 and a second absorbent article 134. Both the first absorbent article 132 and the second absorbent article 134 are illustrated with portions cut away to illustrate underlying features.

The first absorbent article of the first array 130 may have any combination of the features of the absorbent articles described herein. For example, the first absorbent article 132 may include a first body side liner 136, a first back sheet 138, and a first absorbent body 140 positioned between the first body side liner 136 and the first back sheet 138. The first absorbent body 140 defines a first absorbent body length 144. The first absorbent article 132 includes a first body conforming structure 142. The first body conforming structure 142 defines a first body conforming structure length 146 that is at least 50% the first absorbent body length 144. The first body conforming structure 142 defines a first body conforming structure shape 148. The first body conforming structure 142 includes an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width.

The second absorbent article of the first array 130 may have any combination of the features of the absorbent articles described herein. For example, the second absorbent article 134 may include a second body side liner 152, a second back sheet 154, and a second absorbent body 156 positioned between the second body side liner 152 and the second back sheet 154. The second absorbent body 156 defines a second absorbent body length 160. The second absorbent article 134 includes a second body conforming structure 158. The second body conforming structure 158 defines a second body conforming structure length 162 that is at least 50% the second absorbent body length 160. The second body conforming structure 158 defines a second body conforming structure shape 164. The second body conforming structure shape 164 includes an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width.

In the first array 130, the first body conforming structure shape 148 is the same or is substantially the same as the second body conforming structure shape 164. In various embodiments of the first array 130, the first absorbent body length 144 may be greater than, less than, or the same as the second absorbent body length 160. In some embodiments, the first absorbent body length 144 may be at least 10%, at least 15%, or at least 20% greater than the second absorbent body length 160. In various embodiments of the first array 130, the first body conforming structure 142 may define a first body conforming structure area and the second body conforming structure 164 may define a second body conforming structure area wherein the first body conforming structure area is greater than, less than, or the same as the second body conforming structure area.

Figure 7:
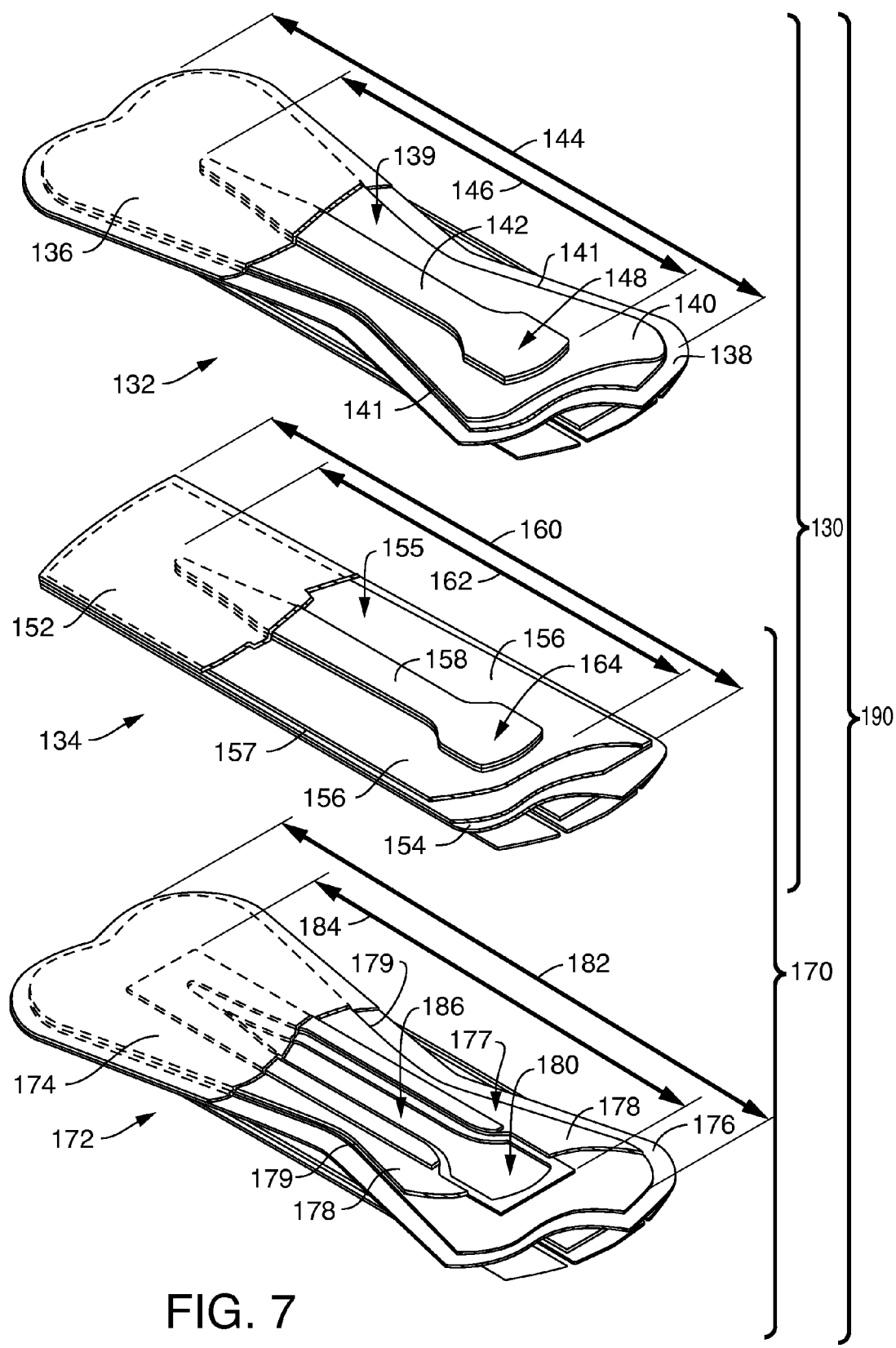
FIG. 7 representatively illustrates exemplary arrays of articles of the present invention.

In various embodiments of the first array 130, the first absorbent body 140 defines a first absorbent body peripheral edge 141 that defines a first absorbent body shape 139. Likewise, the second absorbent body 156 includes a second absorbent body peripheral edge 157 that defines a second absorbent body shape 155. In various embodiments of the first array, the first absorbent body shape may be the same as the second absorbent body shape. In other embodiments of the first array 130, the first absorbent body shape 139 is different than the second absorbent body shape 155. For example, as illustrated in FIG. 7, the first absorbent body shape 139 generally has a curved shape with concave side edges and rounded ends. In comparison, the second absorbent body shape is 155 is generally rectangular.

Referring again to FIG. 7, a second array 170 of products is representatively illustrated. The second array 170 includes the second absorbent article 134 described above and a third absorbent article 172. The third absorbent article 172 is illustrated with portions cut away to illustrate underlying features.

The second absorbent article 134 of the second array 170 may have any combination of the features of the absorbent articles described herein. The third absorbent article 172 of the second array 170 may include any combination of the features of the absorbent articles described herein. For example, the third absorbent article 172 may include a third body side liner 174, a third back sheet 176, and a third absorbent body 178 positioned between the third body side liner 174 and the third back sheet 176. The third absorbent body 178 defines a third absorbent body length 182. The third absorbent article 172 also includes an opening 180 that defines an opening length 184 that is at least 50% the third absorbent body length 182. The opening 180 defines an opening shape 186. The opening shape 186 includes an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width. Other suitable openings are described in the U.S. patent application entitled "Absorbent Article With Recessed Body Conforming Structure" (Ser. No. 13/412,103) by Dieringer et al. and filed on the same date as the present application. The entirety of said application is incorporated herein by reference in its entirety except where contradictory.

In the second array 170, the second body conforming shape 164 is the same or is substantially the same as the opening shape 186. In various embodiments of the second array 170, the second absorbent body length 160 may be greater than, less than, or the same as the third absorbent body length 182. In some embodiments, the second absorbent body length 160 may be at least 10%, at least 15%, or at least 20% greater than the third absorbent body length 182. In some embodiments, the second absorbent body length 160 may be at least 10%, at least 15%, or at least 20% less than the third absorbent body length 182. In various embodiments of the second array 170, the second body conforming structure 158 may define a second body conforming structure area and the opening 180 may define an opening area wherein the second body conforming structure area is greater than, less than, or the same as the opening area.

In various embodiments of the second array 170, the second absorbent body 156 defines a second absorbent body peripheral edge 157 that defines a second absorbent body shape 155. Likewise, the third absorbent body 178 defines a third absorbent body peripheral edge 179 that defines a third absorbent body shape 177. In various embodiments of the second array, the second absorbent body shape may be the same as the third absorbent body shape. In other embodiments of the second array 170, the second absorbent body shape 155 is different than the third absorbent body shape 177. For example, as illustrated in FIG. 7, the second absorbent body shape 155 is generally rectangular. In comparison, the third absorbent body shape 177 is generally a curved shape with concave side edges and rounded ends.

Referring again to FIG. 7, a third array 190 of products is representatively illustrated. The third array 190 includes the first absorbent article 132 described above, the second absorbent article 134 described above, and the third absorbent article 172 described above. However, in various embodiments, the first absorbent article 132, the second absorbent article 134, and/or the third absorbent article 172 of the third array 190 may include any combination of features of the absorbent articles described herein. In the third array 190, the first body conforming structure shape 148, the second body conforming structure shape 164, and the opening shape 186 are the same or are substantially the same. In various embodiments of the third array 190, the first absorbent body length 144 may be greater than, less than, or the same as the second absorbent body length 160 and/or the third absorbent body length 182. In various embodiments of the third array 190, the first absorbent body conforming shape 148 may be the same as or different than the second absorbent body shape 155 and/or the third absorbent body shape 177.

While the invention has been described in detail with respect to specific embodiments thereof, it will be appreciated that those skilled in the art, upon attaining understanding of the foregoing, will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. An absorbent article comprising,
a body side liner,
a back sheet,
an absorbent body positioned between the body side liner and the back sheet wherein the absorbent body defines an absorbent body length, and
a body conforming structure, wherein the body conforming structure is a discrete element positioned between the body side liner and the absorbent body, wherein the body conforming structure defines a body conforming structure length that is at least 50% the absorbent body length and wherein the body conforming structure is aligned with a longitudinal centerline of the absorbent article and wherein the body conforming structure comprises
an anterior portion having a median anterior portion width,
a posterior portion having a median posterior portion width, and
a central portion positioned between the anterior portion and the posterior portion and having a median central portion width, wherein the median anterior portion width is greater than the median central portion width and the median central portion width is greater than the median posterior portion width, and
wherein the anterior portion includes a well having two longitudinal edges, wherein each well longitudinal edge has a section that is generally parallel to the longitudinal centerline, the central portion includes a channel having two longitudinal edges, wherein each channel longitudinal edge has a section that is generally parallel to the longitudinal centerline, and the posterior portion includes a taper wherein the well transitions into the channel via a first convex transition and a concave transition and wherein the channel transitions into the taper via a second convex transition.

2. The absorbent article of claim 1 wherein the body conforming structure defines a longitudinal centerline and a lateral centerline wherein the body conforming structure is symmetric about the longitudinal centerline and asymmetric about the lateral centerline.

3. The absorbent article of claim 2 wherein the lateral centerline divides the body conforming structure into an anterior portion having an anterior portion area and a posterior portion having a posterior portion area wherein the anterior portion area is greater than the posterior portion area.

4. The absorbent article of claim 3 wherein the body side liner is joined to the absorbent body at one or more shaping bonds located around a perimeter of the body conforming structure.

5. The absorbent article of claim 4 wherein the body side liner is joined to the absorbent body at a plurality of shaping bonds proximate the perimeter of the body conforming structure in the posterior portion.

6. The absorbent article of claim 1 further comprising a supplemental body conforming structure positioned between the body side liner and the body conforming structure, wherein the supplemental body conforming structure defines a shape and defines an area, wherein the body conforming structure defines a shape and defines an area, and wherein the supplemental body conforming structure shape is substantially similar to the body conforming structure shape.

7. The absorbent article of claim 6 wherein the supplemental body conforming structure area is less than the body conforming structure area.

8. The absorbent article of claim 1 wherein the body conforming structure is devoid of cellulose fibers or superabsorbent.

9. The absorbent article of claim 8 wherein the body conforming structure comprises a bonded-carded web of polypropylene fibers having a based weight of at least 100 gsm.

10. An absorbent article comprising,
a body side liner,
a back sheet,
an absorbent body positioned between the body side liner and the back sheet wherein the absorbent body defines an absorbent body length, and
a body conforming structure, wherein the body conforming structure is a discrete element positioned between the body side liner and the absorbent body, wherein the body conforming structure is a nonwoven fabric that is substantially devoid of cellulose fibers and superabsorbent material, wherein the body conforming structure defines a body conforming structure length that is at least 50% the absorbent body length, wherein the body conforming structure is aligned with a longitudinal centerline of the absorbent article, and wherein the body conforming structure comprises
an anterior portion having a median anterior portion width,
a posterior portion having a median posterior portion width, and
a central portion positioned between the anterior portion and the posterior portion and having a median central portion width, wherein the median anterior portion width is greater than the median central portion width and the median central portion width is greater than the median posterior portion width, and
wherein the anterior portion includes a well having two longitudinal edges, wherein each well longitudinal edge has a section that is generally parallel to the longitudinal centerline, the central portion includes a channel having two longitudinal edges, wherein each channel longitudinal edge has a section that is generally parallel to the longitudinal centerline, and the posterior portion includes a taper wherein the well transitions into the channel via a first convex transition and a concave transition and wherein the channel transitions into the taper via a second convex transition.

11. The absorbent article of claim 10 wherein nonwoven fabric is a bonded-carded web comprising polypropylene fibers.

12. The absorbent article of claim 11 wherein the body conforming structure has a basis weight of at least 200 gsm.

13. The absorbent article of claim 10 wherein the absorbent article defines a thickness and the body conforming structure defines a thickness that is at least 25% the thickness of the absorbent article.

14. The absorbent article of claim 10 wherein the absorbent body includes a body side absorbent layer and a retention layer positioned between the body side absorbent layer and the backsheet, wherein the body side absorbent layer is an airlaid material and the retention layer comprises 70-90% superabsorbent material.

15. The absorbent article of claim 10 wherein the body conforming structure defines a longitudinal centerline and a lateral centerline wherein the body conforming structure is symmetric about the longitudinal centerline and asymmetric about the lateral centerline and wherein the lateral centerline divides the body conforming structure into an anterior portion having an anterior portion area and a posterior portion having a posterior portion area wherein the anterior portion area is greater than the posterior portion area.

16. The absorbent article of claim 10 further comprising a supplemental body conforming structure positioned between the body side liner and the body conforming structure, wherein the supplemental body conforming structure defines a shape and defines an area, wherein the body conforming structure defines a shape and defines an area, and wherein the supplemental body conforming structure shape is substantially similar to the body conforming structure shape and the supplemental body conforming structure area is less than the body conforming structure area.

\* \* \* \* \*